(12) United States Patent
Ram

(10) Patent No.: US 8,404,262 B2
(45) Date of Patent: Mar. 26, 2013

(54) COMPOSITIONS FOR CONTROL OF MALICIOUS MARINE ANEMONES

(75) Inventor: Sharon Ram, Rehovot (IL)

(73) Assignee: Red Sea Fish Pharm Ltd. (IL)

( * ) Notice: Subject to any disclaimer, the term of this patent is extended or adjusted under 35 U.S.C. 154(b) by 273 days.

(21) Appl. No.: 12/812,743

(22) PCT Filed: Dec. 31, 2008

(86) PCT No.: PCT/IL2008/001702
§ 371 (c)(1),
(2), (4) Date: Jul. 13, 2010

(87) PCT Pub. No.: WO2009/090630
PCT Pub. Date: Jul. 23, 2009

(65) Prior Publication Data
US 2010/0310679 A1   Dec. 9, 2010

(30) Foreign Application Priority Data

Jan. 16, 2008 (IL) .......................................... 188817

(51) Int. Cl.
*A01N 29/00* (2006.01)
*A01N 29/04* (2006.01)
*A01N 33/00* (2006.01)
*A01N 59/00* (2006.01)
*A01N 59/06* (2006.01)
*A01N 59/08* (2006.01)

(52) U.S. Cl. ........ 424/405; 424/677; 424/678; 424/688; 424/696; 514/724; 514/738

(58) Field of Classification Search .................. 424/405, 424/677, 678, 688, 696; 514/724, 738
See application file for complete search history.

(56) References Cited

U.S. PATENT DOCUMENTS

| | | | | |
|---|---|---|---|---|
| 5,096,718 A | * | 3/1992 | Ayres et al. ........................ | 426/9 |
| 7,179,478 B2 | | 2/2007 | Gatto, Jr. | |
| 2002/0086089 A1 | | 7/2002 | Kurzinger | |
| 2006/0073207 A1 | * | 4/2006 | Masters et al. ................ | 424/488 |
| 2007/0119788 A1 | | 5/2007 | Gatto, Jr. | |

FOREIGN PATENT DOCUMENTS

WO    2006/043957 A1    4/2006

OTHER PUBLICATIONS

The Merck Index, 10th edition, Merck & Co., Inc.: Rahway, N.J., 1983, pp. 231 (entry 1647: calcium hydroxide) and pp. 234 (entry 1684: calcium sulfate).*
Siqueira et al. "Antifungal Effects of Endodontic Medicaments," Australian Endodontic Journal, Dec. 2001, 27(3), pp. 112-114.*
About Joes Juice, Author: unknown, JoesJuice, available at joesjuice. com/products.php, on May 2, 2008, pp. 1-2.
Calfo, Aquarium Culture of the Aeolid Nudibranch Berguia—Predator on the Nuisance Anemone Aiptasia, WetWebMedia.com, available at wetwebmedia.com/aiptasiaa ntoine.htm, on May 2, 2008, pp. 1-7.
Carroll et al., Laboratory Culture of Aeolid Nudibranch Berghia verrucicornis (Mollusca Opisthobranchia): Some Aspects of Its Development and Life History, Biol. Bull, No. 179, Dec. 1990, pp. 243-253.
FAQs on Pest Anemones other than Aiptasia, Author: unknown, Web Site Forum, WetWebMedia.com, available at www.wetwebmedia. com/otherpstanemfaqs.htm, on May 2, 2008, pp. 1-8.
Fenner, Aiptasia, My Least Favorite Anemones in Captive Systems, WetWebMedia.com, available at www.wetwebmedia.com/marine/ inverts/cnidaria/antho zoa/aiptasia/aiptasia.htm, on May 2, 2008, pp. 1-7.
Fulton, Proline Control of the feeding reaction of Cordylophora, J. General Physiology, v46, p. 823, Mar. 1, 1963.
Hauter et al., Ways to Eliminate Aiptasia Anemones, About.com, available at saltaquarium.about.com/cs/anemonecare/a/aa100798. htm, on May 2, 2008, pp. 1-2.
International Search Report mailed Mar. 30, 2009 in International Application No. PCT/IL2008/001702, filed Dec. 31, 2008.
Miller et al., How do I get Rid of Aiptasia?, Geocities.com, available at www.geocities.com/CapeCanaveral/Hanger/6279/LettersAiptasia.html?200723, on May 2, 2008, pp. 1-5.
Nagai et al., Feeding Factors for the sea anemone Anthropleura midoril, Marine Biology, Springer Berlin/Heidelberg, Dec. 10, 2004, available at http://www.springerlink.com/content/ th7uhh6j88450445/ on May 2, 2008, pp. 1-2.
K. June Lindstedt, Biphasic Feeding Response in a Sea Anemone: Control by Asparagine and Glutathione, Science, Jul. 23, 1971, pp. 333-334, vol. 173.
Amada Alvarez Reimer et al., Feeding Behavior in the Sea Anemone Calliactis Polypus, Comparative Biochemistry and Physiology. Part A. Comparative Physiology, Elsevier Science Ltd, US, Apr. 1, 1973, pp. 1289-1290, vol. 44A, Pergamon Press, Great Britain.
Database WPI XP002685228, Mar. 22, 1978, Thomson Scientific, London, Great Britain.

* cited by examiner

Primary Examiner — James H. Alstrum-Acevedo
(74) Attorney, Agent, or Firm — Novick, Kim & Lee, PLLC; Harold L. Novick; Jae Youn Kim

(57) ABSTRACT

The present invention relates to improved compositions for controlling marine pest anemones, to methods of application of same, and to kits for the convenient dispensing of such compositions.

41 Claims, No Drawings

COMPOSITIONS FOR CONTROL OF MALICIOUS MARINE ANEMONES

FIELD OF THE INVENTION

The present invention relates to improved compositions for controlling marine pest anemones, to methods of application of same, and to kits for the convenient dispensing of such compositions.

BACKGROUND OF THE INVENTION

Certain anemone species, such as *Aiptasia pallida, A. pulchella, A. insignis, Anemonia majano* and *Boloceroides mcmurrichi* are nuisance pests in reef aquariums. *Aiptasia* species are the most common anemones and generally referred to as glass anemones. These species are very widespread and thrive in shallow, nutrient rich sea water, in tropical and subtropical regions. They are easily and inadvertently introduced into reef aquariums with "live rocks" and corals.

*Aiptasia* anemones are typically light brown in color, have one leg, usually less than 2 inches tall, an oral disc of about ½ inch diameter with a central mouth, and long tapered tentacles. In favorable conditions these anemones may grow to 4 inches tall or more. Although *Aiptasia* are photosynthetic species, in absence of light or in shaded areas they consume organic detritus such as plankton and suspended organic particles in order to reach their energetic demands.

*Aiptasia* anemones are members of the phylum Cnidaria, and, like other Cnidarians, have cells called cnodocytes, otherwise known as canidae cells or nematocysts which contain a stinging mechanism. These cnodocytes release a toxin that is harmful to many of both the invertebrates and corals kept in reef aquariums. Consequently, corals coming into contact with *Aiptasia* generally recede and show signs of distress, and may die.

*Aiptasia* anemones are notoriously difficult to eliminate. They attach themselves to a hard substrate, usually in a crevice thereof, which allows them to quickly withdraw when danger approaches. They have remarkable powers of regeneration so cutting, grinding or smashing these anemones may propagate rather than eliminate them. In addition, they rapidly reproduce asexually through the process known as pedal laceration, which occurs when residual tissue lobes are left behind as the anemone wanders around. These residual lobes quickly develop into new anemones. Furthermore, under adequate conditions, *Aiptasia* anemones can reproduce sexually by releasing thousands of fertilized oocysts to the water. Because *Aiptasia* anemones reproduce quickly, and have extreme regenerating abilities, it is important to eliminate them before they overrun an aquarium in a short period of time.

*Majano* anemones (*Anemonia majano*) are the prettier of the pest anemones found in reef aquariums. *Majano* anemone specimens may be green, red, and even a striking yellow. They are not nearly as prolific as *Aiptasia*, and are somewhat attractive, and therefore are generally less of a nuisance to the reef aquarium hobbyist. They can easily be distinguished from *Aiptasia* because they have bulbous tips on the ends of their tentacles. However, like *Aiptasia*, they have a potent sting and may be harmful to other sessile invertebrates in the aquarium.

*Boloceroides mcmurrichi*, or the Swimming anemone, is another pest anemone similar to *Aiptasia* species. This tan anemone has a short leg and long robust tentacles that may be banded. The oral disk thereof is small and the mouth is white. The swimming anemones reproduce by the same asexual mechanism as *Aiptasia* and by regeneration of detached tentacles. They are photosynthetic creatures, harboring zooxanthellae algae, but can thrive in shaded nutrient rich areas.

There are two basic approaches that are currently used for controlling the pest anemone population in aquaria. One is by natural predation and the other is a chemical approach.

A newly found predator and perhaps the one with the best potential for controlling *Aiptasia* is *Berghia verrucicornis*. This nudibranch was identified in a scientific article by Carrol & Kempf (1). *Berghia verrucicornis* along with most nudibranchs are diet specific. Starter cultures have been exchanged and several aquaculture facilities in the US produce and provide these commercially. However, there are only a limited number of such cultures available and the specimens that can be found are generally too small be put in to a large system and expected to live. Indeed, amongst other dangers, they might fall prey to their very quarry (2). In addition, *Aiptasia*-eating Nudibranch are expensive and difficult to acquire; and they will eat nothing else other than *Aiptasia* so that once there are no *Aiptasia* left in an ecosystem, or so few the nudibranch has trouble finding them, it will starve to death (3-8). Furthermore, a lengthy period may be required to completely eradiate *Aiptasia* by employing the nudibranch (7). Other natural predators of *Aiptasia* species and *Boloceroides mcmurrichi* are the Copperband butterfly fish (*Chelmon rostratus*) and the Peppermint shrimp (*Lysmata wurdemanni*) but there is an inherent danger of these predators eating other, desired tank residents instead of or in addition to the pest anemones.

Chemical approaches to eliminating *Aiptasia* are more widely used. Generally these involve taking a chemical solution of minerals and placing a large dose over the oral disk. One popular method employs an aqueous suspension of calcium hydroxide (lime, kalkwasser) which may be dispensed via a syringe onto or near the *Aiptasia*. The popularity of the approach is partly due to the fact that many reef aquarium hobbyists already have calcium hydroxide on hand for use to maintain/supplement calcium and alkalinity. Additionally, excess calcium hydroxide merely contributes to the calcium concentration in the aquarium, whereas other targeted poisons may be harmful to desired organisms in the aquarium and cannot be left to drift in the water.

Mixed success has been reported with the chemical approach however (4-5, 9), depending upon the chemical used and the method of employing the chemical.

U.S. Pat. No. 7,179,478 and U.S. Patent Application Publication No. 2007/0119788, both to Gatto, which are incorporated by reference for all purposes as if fully set forth herein, disclose a method of killing *Aiptasia* and *Majano* anemones in aquariums, by filling a dispenser with an anemone killing mixture comprising purified water and effective amounts of calcium hydroxide and a non-iodized salt, placing a tip of the filled dispenser near the oral disk of an anemone and dispensing a small amount of the mixture. The calcium hydroxide reacts with the anemone tissues to destroy the anemone. Such a killing mixture, is available commercially under the name Joe's Juice (10). The effectiveness of the mixture is questionable, since, when threatened, the *Aiptasia* often shut or disappear into crevices and getting them to stay open and ingest such mixtures is difficult. It is particularly difficult to inject such mixtures near the mouth of the anemone and to visibly follow where the mixture went to. Consequently, applying the mixture may be quite tedious if many anemones need to be eradicated. In addition, the mixture is highly caustic and some care should be given to handling it for the user's safety and for fear of collateral damage to sensitive cohabitants of aquariums, and large doses may affect the pH of the water.

There is thus a need for an improved composition and method of treatment for controlling anemone pests.

SUMMARY OF THE INVENTION

It is an object of the present invention to provide compositions suitable for controlling the population of pest anemones in reef aquaria and the like.

In one aspect, the present invention relates to compositions for destroying a marine pest anemone comprising: bait that is readily ingestible by the marine pest anemone, an anemonescide for killing the marine pest anemones, and a binder.

In one embodiment of the invention, both bait and binder in the composition comprise agar, and said anemonescide is selected from the group comprising calcium hydroxide and calcium sulphate. Preferably, the anemonescide is calcium hydroxide, which may be provided by mixing a soluble calcium salt, water and an alkali. Typically, said alkali is selected from the group comprising sodium hydroxide and potassium hydroxide. In one embodiment the anemonescide is calcium hydroxide formed by reacting calcium chloride, sodium hydroxide and water.

Preferably, the composition for destroying a marine pest anemone further comprises an anemone desensitizer. Optionally the anemone desensitizer is selected from the list comprising magnesium sulphate, chloral hydrate and menthol.

Preferably, the composition for destroying a marine pest anemone further comprises a feeding inducer of anemones. Optionally the feeding inducer of anemones comprises at least one of the group comprising alanine, glycine, histidine, proline, cysteine, asparagine and reduced glutathione (GSH).

In another embodiment of the invention, bait comprises an anemone foodstuff, the anemonescide is selected from a group comprising calcium hydroxide and calcium sulphate, and said binder is selected from the group comprising: agar, carrageenans, alginates, zein, paraffin, glycerol, glycerin and gelatin. Preferably, the composition further comprises a desensitizer of anemones. Most preferably, the desensitizer comprises magnesium sulphate.

In a second aspect, the present invention is directed to providing a kit comprising a dispenser and any of the compositions described above. Preferably, the dispenser comprises a long-needled syringe. More preferably, the kit further comprises a sealable container for containing said composition.

In a third aspect, the present invention relates to a method for preparation of a composition for destroying a marine pest anemone comprising:

(a) dissolving a binder in water to form a binder solution; and (b) mixing said binder solution with an anemonescide.

Optionally said binder comprises agar.

Alternatively, said composition further comprises a bait and said method comprises mixing in said bait.

In embodiments comprising agar, said agar serves as both a binder and bait, and the method typically comprises dissolving agar in water at a temperature in the range of between 95° C. and 100° C., typically with continuous agitation.

The anemonescide may be formed by:

(i) making up separate aqueous solutions of a soluble calcium salt and an alkali (ii) mixing said calcium salt solution with excess alkali solution.

The step (b) of mixing said agar solution and said anemonescide typically comprises stirring for one hour, ensuring sufficient agar in said composition to bind said calcium hydroxide.

In a second embodiment, the method for preparing the composition comprises the step (a) of dissolving agar in water at between 95° C. and 100° C. with continuous agitation; however the anemonescide is formed by dispersing calcium sulphate in water. Step (b) of mixing the anemonescide and the binder comprises stirring the agar solution and the anemonescide for one hour, with sufficient agar in the composition to fully bind all the calcium sulphate.

Preferably, both methods comprise the additional step of dissolving a desensitizer in water and mixing the solution formed thereof with the binder—anemonescide compositions.

The methods may further comprise the additional step of dissolving a feeding inducer in water and mixing the solution formed thereof with said composition.

In a fourth aspect, the present invention relates to a method for killing a marine anemone, comprising the steps of:

(a) shaking a sealable container containing a composition comprising bait that is readily ingested by said pest marine anemone and an anemonescide that kills marine anemones, until an essentially homogeneous suspension of the composition is formed;

(b) transferring a portion of the suspension to a tip-equipped dispenser to, wherein said portion is an amount sufficient for killing one or more of the anemones;

(c) placing said tip of the loaded dispenser near the mouth of the anemone; and (d) feeding the anemone a fatal dose of the composition.

Typically, at least one of the following limitations is true:
(i) the anemone comprises *Aiptasia;*
(ii) the bait comprises agar;
(iii) the anemonescide is selected from a group comprising calcium hydroxide and calcium sulphate;
(iv) the dispenser is a long-needled syringe;
(v) the fatal dosage is between 0.5 and 1 ml;
(vi) the composition further comprises an anemone desensitizer selected from the group comprising magnesium sulphate, chloral hydrate and menthol; and
(vii) the composition may further comprise a feeding inducer selected from the group comprising: alanine, glycine, histidine, proline, cysteine, asparagine and reduced glutathione (GSH).

DETAILED DESCRIPTION OF THE INVENTION

An object of the present invention is to provide an anemone controlling composition and method for use in reef aquariums, which is fast working and has no significant adverse affects on corals and other aquarium inhabitants.

Another object is to provide a method for controlling anemones in marine aquariums.

In brief, preferred compositions of the invention have been developed for destroying *Aiptasia* and other pest anemones that are generally undesired in reef aquariums. Bringing preferred embodiments into contact with such anemones generally kills them in a fast and efficient manner. It is a particular feature of preferred compositions of the invention that they are easily applied to the anemone to be destroyed, and, generally do not injure other marine life commonly found in marine aquariums.

While some live rocks may be removed from the aquarium and carefully cleansed from *Aiptasia*, the removal procedure is very tedious and upsets other inhabitants of the aquarium and its delicate balance, and sometimes the rocks cannot be removed, perhaps because they are integral to the aquarium structure, or because they contain precious sedentary inhabitants. Furthermore, physical attempts to remove the anemone can result in tissue residuals being left behind which may eventually develop into new anemones.

It is noted that *Aiptasia* anemones often grow on live rocks in aquariums, and quickly vanish into crevices when approached by foreign objects such as syringes. Getting *Aiptasia* to stay open and ingest an anemonescide may be difficult.

Embodiments of the present invention have been developed to overcome this problem by enticing the pest anemones by providing them with compositions containing materials identified by the anemones as food, together with the anemonescide.

It is noted that materials having nutritional value to anemones, henceforth referred to as foodstuffs, may, if not wholly recovered and removed from the aquarium following treatment of the anemones, counterproductively encourage growth and proliferation of the pest anemones. However, other materials, devoid of nutritional value to the anemones, may, nevertheless, be identified by the anemone as being a foodstuff, and thus serve as bait. Such materials, referred to herein as fake foodstuffs, do not promote anemone growth and proliferation.

It has surprisingly been found that anemones readily devour agar, apparently identifying the material as food. Agar is a seaweed derivative that is viscous and sticky. In seawater, agar droplets tend to form into globules, and it has been found suitable for binding anemonescides.

Thus, compositions in accordance with one aspect of the invention comprise an effective amount of an anemonescide and a binder such as agar which also serves as bait. The bait tempts the anemone to ingest same, rather than to retract into crevices, thereby immensely simplifying the killing thereof.

Due to the very effective uptake of such compositions, the effective concentration of the anemonescide therein can be low, which renders the composition relatively safe for use and of minimal effect on the water chemistry of the aquarium.

In another embodiment, the composition comprises agar, at least one soluble calcium salt in excess such as calcium chloride, and a strong alkali such as sodium hydroxide or potassium hydroxide, wherein the calcium salts and the alkali react to form calcium hydroxide, which is weakly soluble and therefore disperses at a slow rate. It has been found that such compositions are readily ingested by the anemone and kill same on ingestion.

In yet another embodiment, the composition comprises agar and a weakly soluble calcium salt such as calcium sulphate.

It has been discovered that compositions comprising agar, calcium chloride, sodium hydroxide and water, form a viscous, milky suspension that has low miscibility in sea water. When small quantities of such compositions are injected into marine aquariums, they form easily visible globules. Thus, such compositions possess the convenient properties of: (a) being easily dispensed to exactly where required via needle syringes and the like, (b) being readily ingested by anemones (c) being lethal to such anemones, even in relatively small amounts, (c) being relatively harmless to other reef inhabitants, (d) eventually dispersing in the aquarium fluid.

In yet other embodiments, compositions of the invention comprise: (i) a foodstuff that is a real anemone nutrient, such as silversides of appropriate size, various kinds of shrimps, defrosted/frozen or dry-frozen cube-foods, fish pastes or planktonic organisms, (ii) a binder such as agar, carrageenans, alginates, zein, gelatin, paraffin, glycerin or glycerol, (iii) an anemonescide, such as calcium hydroxide or calcium sulphate.

The composition according to the invention may usefully comprise further ingredients to facilitate ingestion of the anemonescide. Such ingredients may usefully include desensitizers for desensitizing the anemone to the harmful anemonescide. Examples of such desensitizers include magnesium sulphate, menthol and chloral hydrate, wherein the magnesium ions paralyze the sense organs of the anemone (13). Other useful ingredients may enhance induced feeding. For example, the carnivorous feeding behavior of the sea anemone *Anthopleura midorii* was found (14) to be a sequence of successive feeding motions, which consisted of several separate actions: (a) tentaculation on any solid matter; (b) retention of prey by tentacles; (c) mouth opening; (d) ingestion of food; (e) digestion of food and (f) extrusion of indigestible waste material. Several amino acids were found to induce feeding: alanine, glycine, histidine or asparagine stimulated the retention of artificial food by tentacles, and proline evoked mouth opening. Cysteine or reduced glutathione (GSH) induced food ingestion. Unnatural food stuff such as potato starch was ingestible, if an appropriate amount of a chemical substance was added.

Preferred compositions of the present invention are reef safe. Unlike approaches suggested in the prior art, compositions of the invention do not require injection into the anemone, which is very difficult to achieve. Rather, they are simply applied to pest anemones by being fed to them. It is noted that the composition can be applied with aquarium and/or ambient lights on, and the pest anemones do not retract while being fed. The compositions cause the anemone to shrivel and die, and leaves very little visible residue, so that there is no need to siphon the dead anemone out of tank after application of the composition. The composition has no substantial effect on the water chemistry of the aquarium.

In another aspect, the invention provides a kit comprising a dispenser such as a long-needled syringe and an anemone controlling composition comprising a material identified by the anemone as food and an anemonescide.

In one embodiment, the invention provides a sealable container such as a bottle with a cap that contains the anemone controlling composition, and further provides a dispenser for delivering the composition to the anemones.

Thus the present invention provides improved compositions for killing marine anemones and kits comprising same.

The dispenser used to feed the composition to the undesirable anemones preferably has a plastic flow control tip, and may be provided with an angled tip to provide greater flexibility when feeding. The composition may be administered from the center of the mouth (oral disk) of the *Aiptasia* outward across the mouth until it reaches the base of the tentacles. It is further noted that compositions of the invention do not generally cause breakage of the pest anemone or cause reproduction thereof. Furthermore, in some cases, the user may find additional smaller *Aiptasia* hiding, under or near the larger anemones. These will generally be eliminated by further feeding of all visible *Aiptasia* with the mixture.

EXAMPLES

Example 1

Preparation of Bait-Anemonescide-Desensitizer Composition

Table 1 lists the typical amounts used to prepare a composition including bait, a binder, an anemonescide and a desensitizer, wherein the anemonescide is calcium sulphate or calcium hydroxide formed from calcium chloride and sodium hydroxide, agar serves as both bait and binder, and the desensitizer is magnesium sulphate.

TABLE 1

Ingredients in an agar-anemonescide-desensitizer preparation

| Ingredient | Typical Concentration, g/l | Empirically Determined Effective Concentration range (Min-Max) g/l |
|---|---|---|
| $CaCl_2 \cdot 2H_2O$ | 104 | 10-500 |
| $MgSO_4$ | 2 | 0.5-10 |
| $CaSO_4$ | 30 | 5-150 |
| NaOH | 24 | 5-120 |
| Agar | 3 | 0.5-10 |

Table 1 also lists the empirically determined effective concentration ranges of the various ingredients. While it is believed that less than the minimal effective concentrations might impair the effectiveness of that ingredient, and more than effective concentration will not further improve the effectiveness, it is to be understood that the table is provided by way of enablement and is not to be construed as limiting the invention to the preferred ranges.

A large quantity of a preferred composition of the invention including agar, calcium chloride, sodium hydroxide and magnesium sulphate was prepared as follows:

Agar was dissolved in hot water, and separate aqueous solutions of calcium chloride ($CaCl_2$) magnesium sulphate ($MgSO_4$) and sodium hydroxide (NaOH) were made up as follows:

1. Dissolve 150 g Agar in 5 liters of deionized water (DW) at 95-100° C. with continuous agitation.
2. Mix 5000 g $CaCl_2$ in 10 liters of DW.
3. Dissolve 100 g $MgSO_4$ in 1 liters of DW and add to $CaCl_2$ mixture while continuously mixing
4. Dissolve 1200 g NaOH in 5 liters of DW and add to $CaCl_2$ solution while continuously mixing, to form a mixture of calcium chloride (fully dissolved), magnesium sulphate (partially dissolved), and calcium hydroxide (partially dissolved).
5. Add hot agar solution to the mixture while stirring and make up to 50 liters with DW.
6. Continue stirring the agar-anemonescide-desensitizer mixture for one hour without heating.

It will be appreciated that smaller quantities maybe made up for treating one or two aquariums rather than an industrial quantity as above. Furthermore, other concentrations may be used. In general, however, it is to be noted that in the preparation of the composition the amount of calcium chloride is always selected to be in excess of the amount of sodium hydroxide, so that as a result of the quantitative reaction that occurs between the sodium hydroxide and the calcium chloride, the sodium hydroxide is completely spent and is absent from the composition, while some excess calcium chloride remains in the composition after the completion of the reaction. The calcium in the excess calcium chloride also acts as an anemonescide.

Example 2

Treatment of Pest Anemones with the Agar-Anemonescide Composition

1. Place the composition of Example 1 in a bottle with a screw cap and shake the composition until an essentially homogeneous suspension of the composition is formed. The agar in the shaken composition is in a semi-liquid form and the anemonescide is in suspension.
2. Draw a portion of the suspension of the composition with a syringe with a long needle, wherein the portion is an amount sufficient for killing one or more of the pest anemones.
3. Place the end of the needle of the syringe near the mouth of the anemone.
4. Feed the pest anemone with the composition in an amount sufficient for killing it, typically between 0.5 and 1 ml of the composition. The *Aiptasia* anemone ingests the composition and dies.

It is noted that the composition is fluid and it is easily injectable as and where required using the syringe. Within the aquarium fluid, the mixture does not solidify; however, it thickens, coagulates, and becomes denser, assuming a watery paste or thick liquid glue-like consistency.

When using a composition including only calcium sulphate as an anemonescide to kill pest marine anemones, it may be advantageous to inject the composition not only in the vicinity of the oral disc, but also all over the anemone, to increase the effectiveness of the composition, and use amounts of over 1 ml to kill the anemone.

The scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

REFERENCES

1. D. J. Carroll and S.C. Kempf, 1990: On *Aiptasia* eating Nudibranch. *Biol. Bull.* 179: 243-253
2. Y. Nagai and S. Nagai, 1973: Feeding factors for the sea anemone *Anthopleura midorii*, Marine Biology, Volume 18(1): 55-60
3. The following Internet web pages:
   a. wetwebmedia.com/marine/inverts/cnidaria/anthozoa/aiptasia/aiptasia.htm
   b. wetwebmedia.com/aiptasiaantoine.htm
   c. geocities.com/CapeCanaveral/Hangar/6279/LettersAiptasia.html?200723
   d. reefscapes.net/articles/breefcase/aiptasia_control.html
   e. saltaquarium.about.com/cs/anemonecare/a/aa100798_2.htm
   f. forum.marinedepot.com/Topic36059-4-2.aspx#bm36647
   g. wetwebmedia.com/otherpstanemfaqs.htm
   h. saltaquarium.about.com/cs/anemonecare/a/aa100798.htm
   i. joesjuice.com/products.php
   j. wetwebmedia.com/ca/cav1i3/aiptasia_impressions/aiptaisia_impressions.htm
   k. reefpark.net/forums/index.php?showtopic=25726&hl=gatto
   l. projectdibs.com/forums/archive/index.php?t-1380.html

The invention claimed is:

1. A composition for destroying a marine pest anemone, comprising (a) agar, (b) an anemonescide selected from the group consisting of calcium hydroxide and calcium sulphate, and (c) an anemone desensitizer.
2. The composition of claim 1, wherein said calcium hydroxide is provided from a soluble calcium salt, water and an alkali.

3. The composition of claim 2, wherein said alkali is selected from the group consisting of sodium hydroxide and potassium hydroxide.

4. The composition according to claim 1, wherein said calcium hydroxide comprises calcium chloride, sodium hydroxide and water, whereby the calcium chloride and the sodium hydroxide react to form the calcium hydroxide.

5. The composition according to claim 1, wherein the anemone desensitizer is selected from the group consisting of magnesium sulphate, chloral hydrate and menthol.

6. A kit comprising a dispenser and a composition according to claim 1.

7. The kit of claim 6, wherein said dispenser comprises a syringe.

8. The kit of claim 7, further comprising a sealable container for containing said composition.

9. A method for preparation of the composition of claim 1, the method comprising:
  (a) dissolving the agar in water to form a binder solution;
  (b) mixing said binder solution with the anemonescide; and
  (c) dissolving a desensitizer in water and mixing the solution formed thereof with said composition.

10. The method according to claim 9, wherein
  step (a) comprises dissolving the agar in water at between 95° C. and 100° C. with continuous agitation; said anemonescide being formed by:
    (i) dissolving a soluble calcium salt and an alkali separately in water, wherein said calcium salt is in excess of said alkali; and
    (ii) mixing calcium salt and alkali solutions together to form the calcium hydroxide; and
  step (b) comprises stifling agar solution and said anemonescide for one hour;
wherein said agar is provided in a sufficient amount to bind said calcium hydroxide.

11. The method according to claim 10,
  wherein said anemonescide is formed by dispersing calcium sulphate in water, and
  wherein the sufficient amount of said agar is provided to bind said calcium sulphate.

12. The method of claim 10 further comprising making up an aqueous solution of a feeding inducer and mixing the solution with said composition.

13. A method for killing a pest marine anemone, comprising:
  (a) shaking a sealable container containing the composition of claim 1 until a homogeneous suspension of the composition is formed;
  (b) transferring a dose of said suspension to a tip-equipped dispenser to fill said dispenser with said suspension of said composition, wherein said dose is an amount sufficient for killing said pest anemone;
  (c) placing said tip of said filled dispenser near the mouth of said pest anemone; and
  (d) feeding a fatal dosage of said composition to said pest anemone.

14. The method of claim 13, wherein at least one of the following limitations is true:
  (i) said anemone is *Aiptasia*;
  (ii) said dispenser is a syringe;
  (iii) said dosage is between 0.5 and 1 ml;
  (iv) said composition comprises an anemone desensitizer selected from the group consisting of magnesium sulphate, chloral hydrate and menthol; and
  (v) said composition comprises a feeding inducer selected from the group consisting of: alanine, glycine, histidine, proline, cysteine, asparagine and reduced glutathione (GSH).

15. A composition for destroying a marine pest anemone, comprising (a) agar, (b) an anemonescide selected from the group consisting of calcium hydroxide and calcium sulphate, and (c) a feeding inducer of anemones.

16. The composition according to claim 15, wherein the feeding inducer is selected from the group consisting of: alanine, glycine, histidine, proline, cysteine, asparagine and reduced glutathione (GSH).

17. The composition of claim 15, wherein said calcium hydroxide is provided from a soluble calcium salt, water and an alkali.

18. The composition of claim 17, wherein said alkali is selected from the group consisting of sodium hydroxide and potassium hydroxide.

19. The composition according to claim 15, wherein said calcium hydroxide comprises calcium chloride, sodium hydroxide and water, whereby the calcium chloride and the sodium hydroxide react to form said calcium hydroxide.

20. A kit comprising a dispenser and a composition according to claim 15.

21. The kit of claim 20, wherein said dispenser comprises a syringe.

22. The kit of claim 21, further comprising a sealable container for containing said composition.

23. A method for preparation of the composition of claim 15, the method comprising:
  (a) dissolving the agar in water to form a binder solution;
  (b) mixing said binder solution with the anemonescide; and
  (c) dissolving a desensitizer in water and mixing the solution formed thereof with said composition.

24. The method according to claim 23, wherein
  step (a) comprises dissolving the agar in water at between 95° C. and 100° C. with continuous agitation; said anemonescide being formed by:
    (i) dissolving a soluble calcium salt and an alkali separately in water, wherein said calcium salt is in excess of said alkali; and
    (ii) mixing calcium salt and alkali solutions together to form the calcium hydroxide; and
  step (b) comprises stifling agar solution and said anemonescide for one hour;
wherein said agar is provided in a sufficient amount to bind said calcium hydroxide.

25. The method according to claim 24, wherein said anemonescide is formed by dispersing calcium sulphate in water, and wherein the sufficient amount of said agar is provided to bind said calcium sulphate.

26. The method of claim 24 further comprising making up an aqueous solution of a feeding inducer and mixing the solution with said composition.

27. A method for killing a pest marine anemone, comprising:
  (a) shaking a sealable container containing the composition of claim 15 until a homogeneous suspension of the composition is formed;
  (b) transferring a dose of said suspension to a tip-equipped dispenser to fill said dispenser with said suspension of said composition, wherein said dose is an amount sufficient for killing said pest anemone;
  (c) placing said tip of said filled dispenser near the mouth of said pest anemone; and
  (d) feeding a fatal dosage of said composition to said pest anemone.

28. The method of claim 27, wherein at least one of the following limitations is true:
  (i) said anemone is *Aiptasia*;
  (ii) said dispenser is a syringe;
  (iii) said dosage is between 0.5 and 1 ml;
  (iv) said composition comprises an anemone desensitizer selected from the group consisting of magnesium sulphate, chloral hydrate and menthol; and
  (v) said composition comprises a feeding inducer selected from the group consisting of: alanine, glycine, histidine, proline, cysteine, asparagine and reduced glutathione (GSH).

29. A composition for destroying a marine pest anemone, comprising (a) agar, (b) an anemonescide selected from the group consisting of calcium hydroxide and calcium sulphate, and (c) a binder selected from the group consisting of: carrageenans, alginates, zein, paraffin, glycerol, glycerin and gelatin.

30. The composition of claim 29, wherein said calcium hydroxide is provided from a soluble calcium salt, water and an alkali.

31. The composition of claim 30, wherein said alkali is selected from the group consisting of sodium hydroxide and potassium hydroxide.

32. The composition according to claim 29, wherein said calcium hydroxide comprises calcium chloride, sodium hydroxide and water, whereby the calcium chloride and the sodium hydroxide react to form said calcium hydroxide.

33. A kit comprising a dispenser and a composition according to claim 29.

34. The kit of claim 33, wherein said dispenser comprises a syringe.

35. The kit of claim 34, further comprising a sealable container for containing said composition.

36. A method for preparation of the composition of claim 29, the method comprising:
  (a) dissolving the agar in water to form a binder solution; and
  (b) mixing said binder solution with the anemonescide; and
  (c) dissolving a desensitizer in water and mixing the solution formed thereof with said composition.

37. The method according to claim 36, wherein
  step (a) comprises dissolving the agar in water at between 95° C. and 100° C. with continuous agitation; said anemonescide being formed by:
    (i) dissolving a soluble calcium salt and an alkali separately in water, wherein said calcium salt is in excess of said alkali; and
    (ii) mixing calcium salt and alkali solutions together to form the calcium hydroxide; and
  step (b) comprises stifling agar solution and said anemonescide for one hour;
  wherein said agar is provided in a sufficient amount to bind said calcium hydroxide.

38. The method according to claim 37, wherein said anemonescide is formed by dispersing calcium sulphate in water, and wherein the sufficient amount of said agar is provided to bind said calcium sulphate.

39. The method of claim 37 further comprising making up an aqueous solution of a feeding inducer and mixing the solution with said composition.

40. A method for killing a pest marine anemone, comprising:
  (a) shaking a sealable container containing the composition of claim 29 until a homogeneous suspension of the composition is formed;
  (b) transferring a dose of said suspension to a tip-equipped dispenser to fill said dispenser with said suspension of said composition, wherein said dose is an amount sufficient for killing said pest anemone;
  (c) placing said tip of said filled dispenser near the mouth of said pest anemone; and
  (d) feeding a fatal dosage of said composition to said pest anemone.

41. The method of claim 40, wherein at least one of the following limitations is true:
  (i) said anemone is *Aiptasia*;
  (ii) said dispenser is a syringe;
  (iii) said dosage is between 0.5 and 1 ml;
  (iv) said composition comprises an anemone desensitizer selected from the group consisting of magnesium sulphate, chloral hydrate and menthol; and
  (v) said composition comprises a feeding inducer selected from the group consisting of: alanine, glycine, histidine, proline, cysteine, asparagine and reduced glutathione (GSH).

* * * * *